United States Patent [19]

Tegeler et al.

[11] Patent Number: 4,562,186
[45] Date of Patent: Dec. 31, 1985

[54] (1,2,4-OXADIAZOL-3-YL)ARYLMETHANONES, COMPOSITIONS AND PHARMACEUTICAL USE

[75] Inventors: John J. Tegeler, Bridgewater; Craig J. Diamond, North Wales, Pa.

[73] Assignee: Hoechst-Roussel Pharmaceuticals Inc., Somerville, N.J.

[21] Appl. No.: 693,509

[22] Filed: Jan. 22, 1985

[51] Int. Cl.[4] .................. A61K 31/42; A61K 31/535; C07D 271/06; C07D 413/06
[52] U.S. Cl. ................................... 514/238; 544/138; 544/367; 548/131; 514/240; 514/255; 514/364
[58] Field of Search ................ 544/138, 367; 548/131; 514/238, 240, 255, 364

[56] References Cited

U.S. PATENT DOCUMENTS 4,160,829  7/1979  Heijboer et al. ............... 544/22

FOREIGN PATENT DOCUMENTS 738276  9/1969  Belgium .
738831  9/1969  Belgium .
801913  11/1973  Belgium .

OTHER PUBLICATIONS

Sasaki et al., *Bull. Chem. Soc. Japan*, vol. 44 (1971), pp. 185–189.
Merckx, *Chemical Abstracts*, vol. 42 (1948), 4577f.
Merckx, *Chemical Abstracts*, vol. 44 (1950), 3490e.

Primary Examiner—Robert W. Ramsuer
Attorney, Agent, or Firm—Tatsuya Ikeda

[57] ABSTRACT

There are disclosed novel compounds having the formula

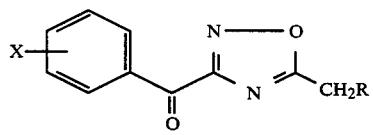

where X is hydrogen, halogen (F, Cl, Br or I), loweralkyl or loweralkoxy; and R is —CH, —CONH$_2$, —COOCH(CH$_3$)$_2$, —COOH, —COO(CH$_2$)$_4$Cl,

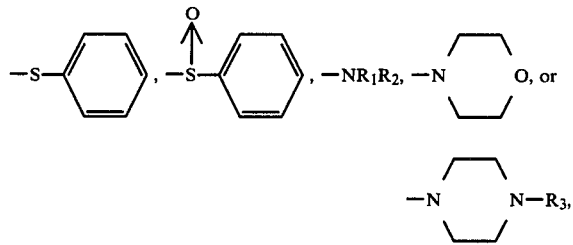

$R_1$ and $R_2$ being independently hydrogen or lower alkyl and $R_3$ being

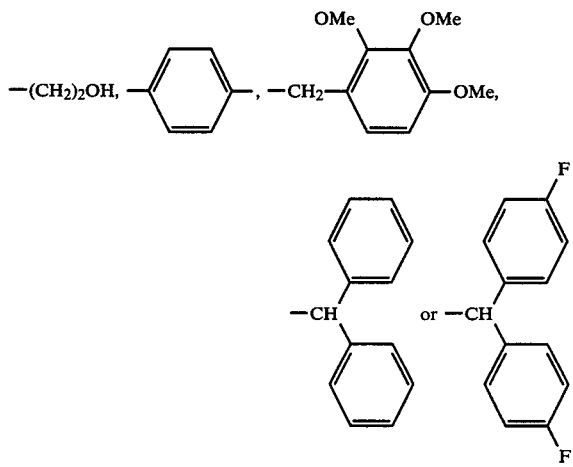

an optical antipode thereof or a pharmaceutically acceptable acid addition salt thereof, which are useful as antihypertensive, analgesic and antiinflammatory agents, methods for synthesizing them, and pharmaceutical compositions comprising an effective amount of such a compound.

85 Claims, No Drawings

(1,2,4-OXADIAZOL-3-YL)ARYLMETHANONES, COMPOSITIONS AND PHARMACEUTICAL USE

This invention relates to novel compounds of the formula

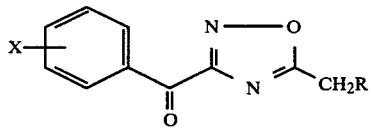

where X is hydrogen, halogen (F, Cl, Br or I), loweralkyl or loweralkoxy; and R is —CN, —CONH$_2$, —COOCH(CH$_3$)$_2$, —COOH, —COO(CH$_2$)$_4$Cl,

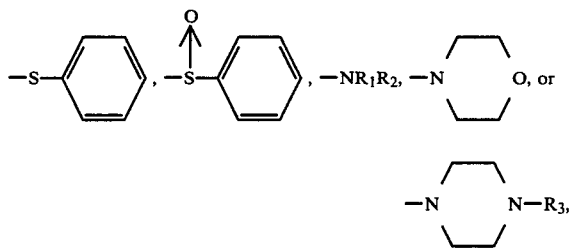

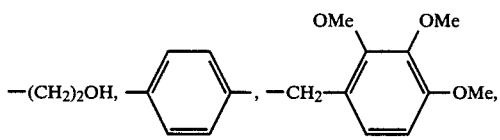

R$_1$ and R$_2$ being independently hydrogen or loweralkyl and R$_3$ being

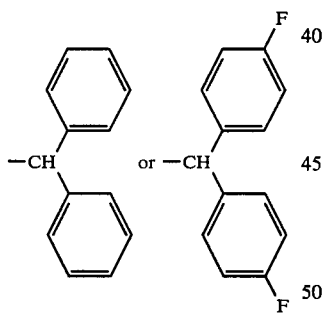

an optical antipode thereof or a pharmaceutically acceptable acid addition salt thereof, which are useful as antihypertensive, analgesic and antiinflammatory agents, methods for synthesizing them, and pharmaceutical compositions comprising an effective amount of such a compound.

Unless otherwise stated or indicated, the term loweralkyl denotes a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched chain pentoxy and hexoxy.

Unless otherwise stated or indicated, the term halogen shall mean fluorine, chlorine, bromine or iodine.

The compounds of the present invention are prepared by following one or more of the steps described below. Throughout the description of the synthetic steps, the definitions of X, R, R$_1$, R$_2$ and R$_3$ and n are as given above unless otherwise stated or indicated.

STEP A

A compound of Formula III below is prepared by a cyclo-addition reaction between a compound of Formula II and malononitrile.

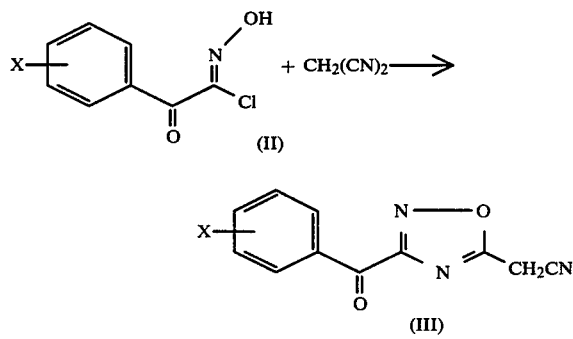

Typically, said cyclo-addition reaction is conducted at a temperature of 100°–150° C. in a suitable medium including aromatic hydrocarbons such as toluene, xylene or the like.

STEP B

A compound of Formula IV below is prepared by reacting compound III with concentrated sulfuric acid and then reacting the resultant product with water. The first step is typically conducted by preparing a solution of compound III in a large excess of concentrated (e.g. 98%) sulfuric acid and stirring the solution at a temperature of 10°–40° C. The second step is typically conducted by slowly pouring said solution into ice water at the end of the first step.

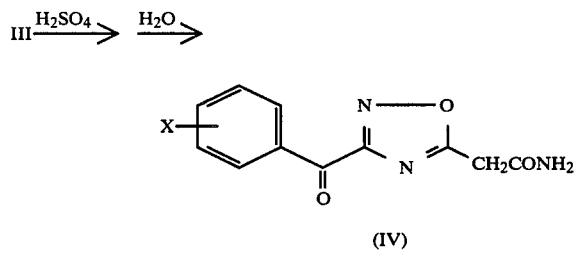

STEP C

A compound of Formula V below is prepared by reacting compound IV with isopropanol. Typically said reaction is conducted by preparing a solution of compound IV in excess isopropanol, saturating the solution with hydrogen chloride gas and stirring or refluxing the solution at a temperature of about 70°–83° C.

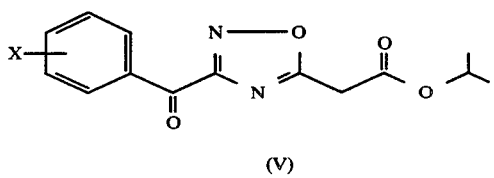

(V)

STEP D

Alternatively, compound V can also be prepared by reacting compound III with isopropanol in the presence of an acid such as hydrogen chloride and then reacting the resultant product with water. Typically, the first step is conducted by preparing a solution of compound III in excess dry isopropanol, saturating the solution with hydrogen chloride gas and stirring or refluxing the solution at a temperature of about 70°–83° C. The second step is typically conducted by pouring said solution into cold water at the end of the first step.

STEP E

A compound of Formula VI below is prepared by hydrolyzing compound V. Said hydrolysis is typically conducted by preparing a solution of compound V in excess concentrated sulfuric acid, stirring the solution at a temperature of 0°–30° C. and thereafter pouring it into ice water.

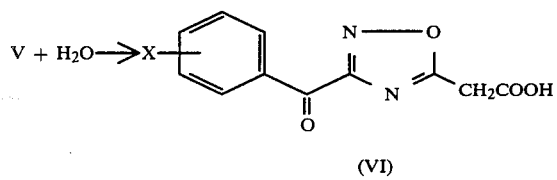

(VI)

STEP F

A compound of Formula VII below is prepared by reacting compound III with ethanethiol and hydrogen chloride in tetrahydrofuran. Typically said reaction is conducted by preparing a solution of compound III and ethanethiol in tetrahydrofuran, saturating the solution with hydrogen chloride gas and stirring the solution at a temperature between about −10° C. and +10° C.

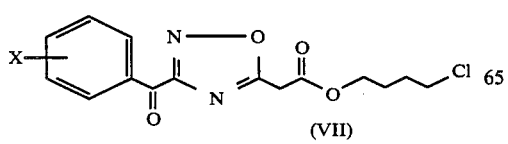

(VII)

STEP G

A compound of Formula VIII below is prepared by a cyclo-addition reaction between compound II and chloroacetonitrile. Said cyclo-addition is conducted in substantially the same manner as STEP A.

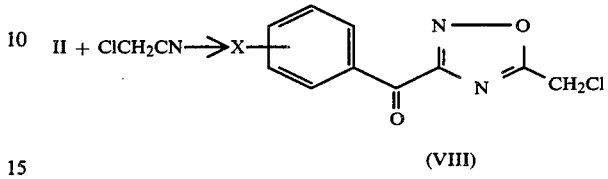

(VIII)

STEP H

A compound of Formula IX below is prepared by reacting compound VIII with phenyl mercaptan.

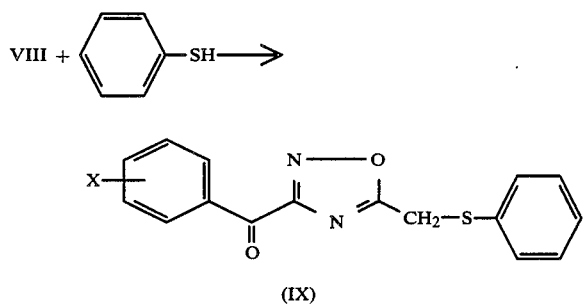

(IX)

Said reaction is usually conducted in the presence of a base such as triethylamine, pyridine, sodium hydride or the like in a suitable solvent including acetone, ethereal compounds such as diethyl ether, tetrahydrofuran, dioxane or the like, and dimethylformamide at a temperature of about 20°–60° C.

STEP I

A compound of Formula X below is prepared by oxidizing compound IX with a suitable peroxy compound such as, for instance, m-chloroperoxybenzoic acid.

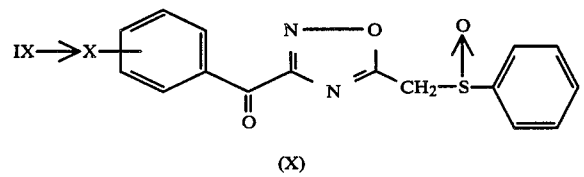

(X)

Typically, said oxidation reaction is conducted in a suitable solvent such as dichloromethane at a low temperature of from about −80° C. to about −60° C.

STEP J

A compound of Formula XI below is prepared by reacting compound VIII with an amine or ammonia of the formula $HNR_1R_2$.

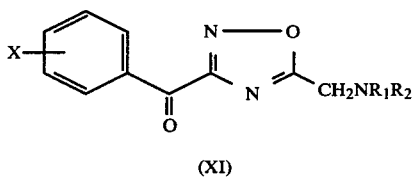

(XI)

Typically, when said amine is a gas as in the case of dimethylamine, the amine gas is bubbled into a suitable solvent including alcohols such as methanol, ethanol and propanol, ethereal compounds such as diethyl ether, tetrahydrofuran and dioxane and mixtures thereof, in order to saturate the solvent with the amine and then the resultant saturated solution is added to a solution of compound VI in a suitable solvent such as those mentioned above. When said amine is a liquid, the reaction mixture is prepared simply by dissolving the two reactants in a suitable solvent such as those mentioned above. The reaction is usually conducted at a temperature of about 20°–100° C.

STEP K

A compound of Formula XII below is prepared by reacting compound VIII with morpholine.

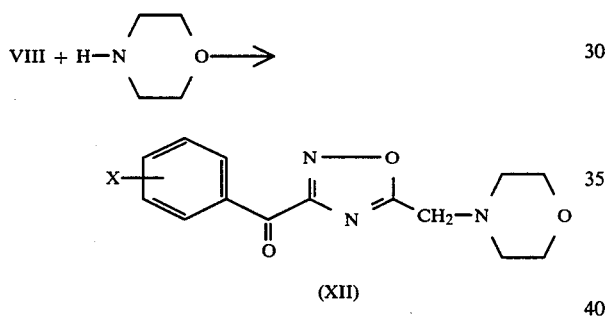

(XII)

Said reaction is conducted in substantially the same manner as described in STEP J.

STEP L

A compound of Formula XIII below is prepared by reacting compound VIII with a compound of Formula XIV.

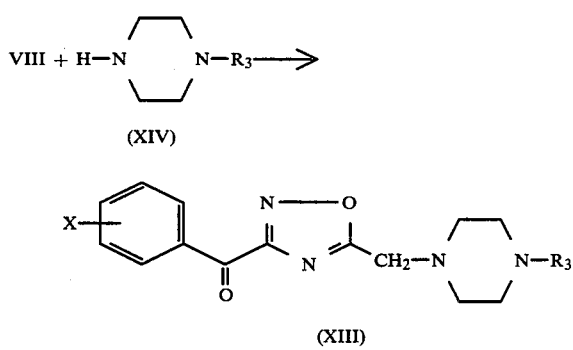

(XIV)

(XIII)

Said reaction is conducted in substantially the same manner as described in STEP J.

The compounds of the present invention are useful as antihypertensive agents due to their ability to depress blood pressure in mammals. Antihypertensive activity is measured in the spontaneous hypertensive rat by the indirect tail cuff method described in "Methods in Pharmacology", A. Schwartz, Ed., Vol. I, Appleton-Century Crofts, New York, N.Y., 1971, p. 135. In this procedure a group of five animals are treated orally for three days with the test compound in relation to a control group of the same number. The drop in blood pressure is measured on the third day following administration. The antihypertensive activities of some of the compounds, expressed as a decrease in mean arterial blood pressure (in mm Hg), are given in Table I along with the activity of a standard compound.

The compounds of the present invention are also useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med., 95, 729 (1957)]. Table I shows a result of the test of the analgesic activities of some of the compounds of this invention along with the activity of a standard compound.

The compounds of the present invention are also useful as antiinflammatory agents due to their ability to suppress inflammation in mammals. The activity of the compounds is demonstrated in the carrageenin induced raw paw edema antiinflammatory assay [Proc. Soc. Exptl. Biol. Med., III 544 (1962), J. Pharmacol. Exp., 141 (1963)]. The results of the antiinflammatory test of some of the compounds of this invention are given in Table I along with a result for a standard compound.

TABLE I

|  | SHR mm dec. in BP @ 50 mg/kg p.o. | CPE % dec. @ 100 mg/kg p.o. | PQW % dec. |
|---|---|---|---|
| 5-Phenylthiomethyl-3-(4-toluoyl)-1,2,3-oxadiazole | — | 33 | 49 @ 25 mg/kg p.o. |
| 3-(4-Chlorobenzoyl)-5-phenylthiomethyl-1,2,4-oxadiazole | — | 43 | 41 @ 25 mg/kg p.o. |
| 3-Benzoyl-5-(phenyl-sulfinyl)methyl-1,2,4-oxadiazole | — | 18 | 49 @ 25 mg/kg p.0. |
| [5-(4-Phenylpiperazin-1-yl)methyl-1,2,4-oxadiazol-3-yl]-4-fluorophenylmethanone | 31 | — | 31 @ 20 mg/kg s.c. |
| (5-Dimethylamino-methyl-1,2,4-oxadiazol-3-yl)-4-fluorophenyl-methanone maleate | 32 | 14 | — |
| [5-[4-(4,4'-Difluoro-benzhydryl-piperazin-1-yl]methyl-1,2,4-oxadiazol-3-yl]phenyl-methanone dimaleate | — | — | 48 @ 20 mg/kg s.c. |
| [5-[4-(4,4'-Difluoro-benzhydryl)piperazin-1-yl]methyl-1,2,4-oxadiazol-3-yl]-4-methoxy-phenylmethanone dimaleate | 31 | — | 63 @ 20 mg/kg s.c. |
| [5-[4-(2,3,4-Trimethoxy-benzyl)piperazin-1-yl]methyl-1,2,4-oxadiazol-3-yl]-4-tolylmethanone dimaleate | — | — | 60 @ 20 mg/kg s.c. |
| (3-Benzoyl-1,2,4-oxadiazol-5-yl)acetonitrile | — | 32 | 31 @ 20 mg/kg s.c. |
| [3-(4-Chlorobenzoyl)-1,2,4-oxadiazol-5-yl]-acetamide | — | 35 | 30 @ 20 mg/kg s.c. |
| [3-(4-Chlorobenzoyl)-1,2,4-oxadiazol-5-yl]- | — | — | 47 @ 25 mg/kg s.c. |

TABLE I-continued

| | SHR mm dec. in BP @ 50 mg/kg p.o. | CPE % dec. @ 100 mg/kg p.o. | PQW % dec. |
|---|---|---|---|
| acetic acid | | | |
| (3-Benzoyl-1,2,4-oxadiazol-5-yl)acetic acid | — | 19 | 59 @ 25 mg/kg s.c. |
| [3-(4-Toluoyl)-1,2,4-oxadiazol-5-yl]-acetonitrile | — | — | 48 @ 25 mg/kg s.c. |
| Isopropyl [3-(4-toluoyl)-1,2,4-oxadiazol-5-yl]-acetate | — | — | 43 @ 25 mg/kg s.c. |
| [3-(4-Fluorobenzoyl)-1,2,4-oxadiazol-5-yl]-acetamide | — | — | 54 @ 25 mg/kg s.c. |
| Isopropyl [3-(4-fluorobenzoyl)-1,2,4-oxadiazol-5-yl]acetate | — | — | 46 @ 25 mg/kg s.c. |
| [3-(4-Methoxybenzoyl)-1,2,4-oxadiazol-5-yl]-acetamide | — | — | 75 @ 25 mg/kg s.c. |
| (prior art compounds) | | | |
| Methyldopa | 40 | — | — |
| Aspirin | | ED$_{50}$ = 130 mg/kg p.o. | |
| Propoxyphene | | | ED$_{50}$ = 24.6 mg/kg, p.o. |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxidel; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied to be between 0.5 and about 30% of the weight thereof. The amount of active compound in such compositions and preparations according to the present invention are prepared so that a parenteral dosage unit contains between 0.5 to 100 milligrams of active compound.

The solutions or suspension may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
(3-Benzoyl-1,2,4-oxadiazol-5-yl)acetonitrile
(3-Benzoyl-1,2,4-oxadiazol-5-yl)acetamide
4-Chlorobutyl(3-benzoyl-1,2,4-oxadiazol-5-yl)acetate
Isopropyl(3-benzoyl-1,2,4-oxadiazol-5-yl)acetate
[3-(4-Chlorobenzoyl)-1,2,4-oxadiazol-5-yl]acetamide
[3-(4-Chlorobenzoyl)-1,2,4-oxadiazol-5-yl]acetonitrile
[3-(4-Chlorobenzoyl)-1,2,4-oxadiazol-5-yl]acetic acid
(3-Benzoyl-1,2,4-oxadiazol-5-yl)acetic acic
Isopropyl[3-(4-chlorobenzoyl)-1,2,4-oxadizol-5-yl]acetate
[3-(4-Toluoyl)-1,2,4-oxadiazol-5-yl]acetonitrile
[3-(4-Toluoyl)-1,2,4-oxadiazol-5-yl]acetamide
[3-(4-Fluorobenzoyl)-1,2,4-oxadiazol-5-yl]acetonitrile
Isopropyl[3-(4-toluoyl)-1,2,4-oxadiazol-5-yl]acetate
[3-(4-Toluoyl)-1,2,4-oxadiazol-5-yl]acetic acid
[3-(4-Fluorobenzoyl)-1,2,4-oxadiazol-5-yl]acetamide
Isopropyl[3-(4-fluorobenzoyl)-1,2,4-oxadiazol-5-yl]acetate
[3-(4-Fluorobenzoyl)-1,2,4-oxadiazol-5-yl]acetic acid
5-Phenylthiomethyl-3-(4-toluoyl)-1,2,4-oxadiazole
3-(4-Chlorobenzoyl)-5-phenylthiomethyl-1,2,4-oxadiazole
[3-(4-Methoxybenzoyl)-1,2,4-oxadiazol-5-yl]acetonitrile
[3-(4-Methoxybenzoyl)-1,2,4-oxadiazol-5-yl]acetamide
Isopropyl[3-(4-methoxybenzoyl)-1,2,4-oxidiazol-5-yl]acetate
5-(Phenylsulfinyl)methyl-3-(4-toluoyl)-1,2,4-oxadiazole
3-Benzoyl-5-phenylthiomethyl-1,2,4-oxadiazole 3-Benzoyl-5-(phenylsulfinyl)methyl-1,2,4-oxadiazole
3-(4-Chlorobenzoyl)-5-(phenylsulfinyl)methyl-1,2,4-oxadiazole
[3-(4-Methoxybenzoyl)-1,2,4-oxadiazol-5-yl]acetic acid
[5-(4-Phenylpiperazin-1-yl)methyl-1,2,4-oxadiazol-3-yl]-4-fluorophenylmethanone
(5-Dimethylaminomethyl-1,2,4-oxadiazol-3-yl)-4-fluorophenylmethanone maleate
[5-(Morpholin-4-yl)methyl-1,2,4-oxadiazol-3-yl]-4-fluorophenylmethanone hydrochloride
[5-(4-beta-Hydroxyethylpiperazin-1-yl)methyl-1,2,4-oxadiazol-3-yl]-4-fluorophenylmethanone dimaleate
[5-[4-(4,4'-Difluorobenzhydryl)piperazin-1-yl]methyl-1,2,4-oxadiazol-3-yl]phenylmethanone dimaleate
[5-(4-Benzhydrylpiperazin-1-yl)methyl-1,2,4-oxadiazol-3-yl]phenylmethanone dimaleate
[5-[4-(2,3,4-Trimethoxybenzyl)piperazin-1-yl]methyl-1,2,4-oxadiazol-3-yl]phenylmethanone dimaleate
[5-(4-Benzhydrylpiperazin-1-yl)methyl-1,2,4-oxadiazol-3-yl]-4-fluorophenylmethanone dimaleate
[5-(4-Benzhydrylpiperazin-1-yl)methyl-1,2,4-oxadiazol-3-yl]-4-methoxyphenylmethanone dimaleate
[5-[4-(4,4'-Difluorobenzhydryl)piperazin-1-yl]methyl-1,2,4-oxadiazol-3-yl]-4-methoxyphenylmethanone dimaleate
[5-[4-(2,3,4-Trimethoxybenzyl)piperazin-1-yl]methyl-1,2,4-oxadiazol-3-yl]-4-tolylmethanone dimaleate The following examples are given for illustrative purposes and are not to be considered as limiting the invention disclosed herein. All temperatures are given in degrees Celcius.

EXAMPLE 1

(3-Benzoyl-1,2,4-oxadiazol-5-yl)acetonitrile

A mixture of 15 g of -chloroisonitrosoacetophenone, 54 g of malononitrile and 500 ml of toluene was refluxed with mechanical stirring under $N_2$ for 6 hours. The resulting mixture was stirred at room temperature overnight. The resulting suspension was decanted and the solids washed with toluene. The toluene was removed in vacuo and the resulting oil was taken up in $Et_2O$. This solution was washed with water (5x) and saturated NaCl solution and dried over $MgSO_4$. The ethereal solution was concentrated to about 50 ml and cooled to precipitate 3.9 g of a solid, m.p. 95°–97°. Recrystallization from $CH_2Cl_2$/cyclohexane gave 3.5 g (20%) of a solid, m.p. 96.5°–97.5°.

ANALYSIS Calculated for $C_{11}H_7N_3O_2$: 61.97%C; 3.31%H; 19.71%N; Found: 61.79%C; 3.40%H; 19.57%N.

EXAMPLE 2

[3-(4-Fluorobenzoyl)-1,2,4-oxadiazol-5-yl]acetonitrile

A mixture of 4-fluorophenylglyoxylohydroxamyl chloride (121 g) and malononitrile (396 g) was dissolved in toluene (2600 ml) and refluxed under $N_2$ for 20 hours. The toluene was removed in vacuo and the excess malononitrile was distilled away using a rotary evaporator under a high vacuum. The residue (143 g) was purified by high pressure liquid chromatography using $CH_2Cl_2$ as an eluent to afford 81 g (59%) of an oil which solidified upon standing. The crude solid (58.5 g) was triturated with anhydrous $Et_2O$ (2×75 ml), filtered and dried to yield 32.4 g (32%) of a solid, m.p. 78°–80°.

ANALYSIS: Calculated for $C_{11}H_6FN_3O_2$: 57.15%C; 2.62%H; 18.17%N; Found: 56.88%C; 2.73%H; 18.11%N.

EXAMPLE 3

[3-(4-Chlorobenzoyl)-1,2,4-oxadiazol-5-yl]acetonitrile

A mixture of 38 g of 4-chlorophenylglyoxylohydroxamyl chloride and 112 g of malononitrile in one liter of toluene was refluxed for 48 hours under $N_2$. The cooled mixture was filtered and concentrated in vacuo. The residue was taken up in $Et_2O$, washed with water (8×) and brine, and dried over $MgSO_4$. Concentration gave an oil which was purified by high pressure liquid chromatography using 5% hexane/$CH_2Cl_2$ as an eluent to give 12 g (28%) of an oil which solidified on standing, m.p. 81°–84°.

ANALYSIS: Calculated for $C_{11}H_6ClN_3O_2$: 53.35%C; 2.44%H; 16.97%N; Found: 53.56%C; 2.47H; 16.64%N.

EXAMPLE 4

[3-(4-Toluoyl)-1,2,4-oxadiazol-5-yl]acetonitrile

A mixture of 125 g of 4-tolylglyoxylohydroxamyl chloride, 420 g of malononitrile and 3000 ml toluene was refluxed for 18 hours under $N_2$. The cooled mixture was filtered and concentrated. The residue was taken up in $Et_2O$, washed with water (8×) and brine, and dried over $MgSO_4$. Concentration to about 200 ml and cooling precipitated 33.2 g of a solid, m.p. 78°–78°. A solution of this material in $CH_2Cl_2$ (1000 ml) was stirred with and decanted from 30 g of silica gel. Concentration gave 27.3 g (19%) of a solid, m.p. 76°–78°.

ANALYSIS: Calculated for $C_{11}H_9N_3O_2$: 63.43%C; 3.99%H; 18.49%N; Found: 63.11%C; 4.10%H; 18.41%N.

EXAMPLE 5

[3-(4-Methoxybenzoyl)-1,2,4-oxadiazol-5-yl]acetonitrile

A mixture of 4-methoxphenylglyoxyolhydroxamyl chloride (170 g), malononitrile (335 g) and toluene (2500 ml) was refluxed under $N_2$ for 20 hours. The toluene was removed in vacuo. The residue was dissolved in ether (2 liters), washed with water (6×1 liter), and filtered through alumina, and the volatiles were removed in vacuo. The residue (178 g) was purified twice by high pressure liquid chromatography (2% ethyl acetate/$CH_2Cl_2$) to afford 75 g of a semi-solid residue. The residue was triturated with anhydrous $Et_2O$ (3×100 ml), filtered, and dried to yield 55 g (28%) of a granular solid, m.p. 92°–94°.

ANALYSIS: Calculated for $C_{12}H_9N_3O_3$: 59.26%C; 3.74%H; 17.27%N; Found: 59.25%C; 3.82%H; 17.38%N.

EXAMPLE 6

(3-Benzoyl-1,2,4-oxadiazol-5-yl)acetamide

A solution of 5.0 g of 3-benzoyl-1,2,4-oxadiazol-5-yl)acetonitrile in 50 ml 98% $H_2SO_4$ was stirred at room temperature overnight. The resulting solution was added slowly to a liter of ice water with mechanical stirring to precipitate a solid. The collected solid was washed with excess water and dried at 90° under high vacuum to give 4.9 g (90%) of a powder, m.p. 155.5°–157.5°.

ANALYSIS: Calculated for $C_{11}H_9N_3O_3$: 57.14%C; 3.92%H; 18.17%N; Found: 57.17%C; 3.96%H; 18.12%N.

EXAMPLE 7

[3-(4-Fluorobenzoyl)-1,2,4-oxadiazol-5-yl]acetamide

A solution of [3-(4-fluorobenzoyl)-1,2,4-oxadiazol-5-yl]acetonitrile (5.0 g) in 98% $H_2SO_4$ (50 ml) was stirred at room temperature for 3 hours. The resulting solution was added slowly to a liter of ice water with mechanical stirring. The precipitated solid was collected by filtration and washed with water (5×300 ml) and cold isopropanol (3×150 ml). The amide was dried in vacuum to yield 5.2 g (96%) of a powder, m.p. 197°–199°.

ANALYSIS: Calculated for $C_{11}H_8FN_3O_3$: 53.02%C; 3.24%H; 16.85%N; Found: 52.84%C; 3.27%H; 16.98%N.

EXAMPLE 8

[3-(4-Chlorobenzoyl)-1,2,4-oxadiazol-5-yl]acetamide

A mixture of 2.8 g of [3-(4-chlorobenzoyl)-1,2,4-oxadiazol-5-yl]acetonitrile and 25 ml of 98% $H_2SO_4$ was stirred at room temperature overnight. The resulting solution was added slowly to 500 ml of ice water with mechanical stirring to precipitate a solid. The collected solid was washed with excess water and dried in vacuo to give 2.6 g of a solid. Recrystallization from isopropanol yielded 2.12 g (71%) of crystals, m.p. 156°–158°.

ANALYSIS: Calculated for $C_{11}H_8ClN_3O_3$: 49.73%C; 3.04%H; 15.82%N; Found: 50.14%C; 3.24%H; 15.53%N.

EXAMPLE 9

[3-(4-Toluoyl)-1,2,4-oxadiazol-5-yl]acetamide

A mixture of 23 g of [3-(4-toluoyl)-1,2,4-oxadiazol-5-yl]acetonitrile and 200 ml of 98% $H_2SO_4$ was stirred at room temperature overnight. The resulting solution was added slowly to 3000 ml of ice water with mechanical stirring to precipitate a solid. The collected solid was washed with excess water and 600 ml of cold isopropanol, and dried in vacuo to give 21 g (86%) of a solid, m.p. 169°–171°.

ANALYSIS: Calculated for $C_{12}H_{11}N_3O_3$: 58.77%C; 4.52%H; 17.13%N; Found: 58.81%C; 4.52%H; 17.23%N.

EXAMPLE 10

[3-(Methoxybenzoyl)-1,2,4-oxadiazol-5-yl]acetamide

A solution of [3-(4-methoxybenzoyl)-1,2,4-oxadiazol-5-yl]acetonitrile (5.0 g) in 98% $H_2SO_4$ (50 ml) was stirred at room temperature for 3 hours. The resulting solution was added slowly to ice water (500 ml) with stirring. The precipitated solid was collected by filtration, and washed with water (5×300 ml) and isopropanol (25 ml). The crude dry amide (3.6 g) was crystallized from EtOH (100 ml) to yield 2.6 g (48%) of needles, m.p. 149°–150°.

ANALYSIS: Calculated for $C_{12}H_{11}N_3O_4$: 55.17%C; 4.25%H; 16.08%N; Found: 55.03%C; 4.32%H; 16.26%N.

EXAMPLE 11

Isopropyl(3-benzoyl-1,2,4-oxadiazol-5-yl)acetate

A mixture of 9.2 g of (3-benzoyl-1,2,4-oxadiazol-5-yl)acetamide in 300 ml isopropanol was saturated with HCl gas. The resulting mixture was warmed to 70° and maintained there for 11 hours. The resulting cooled mixture was filtered and diluted with 400 ml water. Extraction with $Et_2O$ (3×300 ml), washing the organics with a saturated $NaHCO_3$ solution, drying over $MgSO_4$, filtration and concentration gave 10.1 g of an oil. Purification of 9.8 g of this oil by high pressure liquid chromatography with 20% hexane/$CH_2Cl_2$ used as an eluent gave 7.0 g (64%) of an oil.

ANALYSIS: Calculated for $C_{14}H_{14}N_2O_4$: 61.30%C; 5.14%H; 10.22%N; Found: 61.59%C; 5.19%H; 10.09%N.

EXAMPLE 12

Isopropyl[3-(4-fluorobenzoyl)-1,2,4-oxadiazol-5-yl]acetate

A mixture of 19.6 g of [3-(4-fluorobenzoyl)-1,2,4-oxadiazol-5-yl]-acetonitrile and isopropanol (500 ml) was saturated with HCl gas. The resulting solution was refluxed for 6 hours, cooled, and poured into cold $H_2O$ (1000 ml) with stirring. The aqueous mixture was extracted with $Et_2O$ (4×200 ml). The organics were washed with water until neutral, dilute $NaHCO_3$ and saturate NaCl, dried over $Na_2SO_4$, and concentrated in vacuo to give 23 g of an oil. The crude ester was purified by high pressure liquid chromatography (15% ethyl acetate/hexane) to yield 20 g (80%) of an oil.

ANALYSIS: Calculated for $C_{14}H_{13}FN_2O_4$: 57.53%C; 4.49%H; 9.58%N; Found: 57.65%C; 4.65%H; 9.49%N;

EXAMPLE 13

Isopropyl[3-(4-chlorobenzoyl)-1,2,4-oxodiazol-5-yl]acetate

A mixture of 7.2 g of [3-(4-chlorobenzoyl)-1,2,4-oxadiazol-5-yl]acetamide and 200 ml of anhydrous isopropanol was saturated with HCl gas. The resulting solution was warmed at about 70° overnight. The cooled mixture was filtered, diluted with water and extracted with $Et_2O$. The extracts were washed with saturated $NaHCO_3$ solution, dried over $MgSO_4$ and concentrated to give 8.1 g of an oil. Purification by HPLC with 20% hexane/$CH_2Cl_2$ as an eluent gave 5.9 g (71%) of an oil.

ANALYSIS: Calculated for $C_{14}H_{13}ClN_2O_4$: 54.46%C; 4.24%H; 9.08%N; Found: 54.58%C; 4.23%H; 9.19%N.

EXAMPLE 14

Isopropyl[3-(4-toluoyl)-1,2,4-oxadiazol-5-yl]acetate

A mixture of 17 g of [3-(4-toluoyl-1,2,4-oxadiazol-5-yl]acetamide and 500 ml of isopropanol was saturated with HCl gas. The resulting solution was refluxed overnight. The cooled mixture was filtered, diluted with water (700 ml) and extracted with $Et_2O$ (3×). The organics were washed with saturated $NaHCO_3$ solution, dried over $MgSO_4$, and concentrated to an oil. This material was purified by high pressure liquid chromatography with 15% ethyl acetate/hexane as an eluent to give 11.2 g (56%) of an oil.

ANALYSIS: Calculated for $C_{15}H_{16}N_2O_4$: 62.49%C; 5.59%H; 9.72%N; Found: 62.60%C; 5.72%H; 9.68%N.

EXAMPLE 15

Isopropyl[3-(4-methoxybenzoyl)-1,2,4-oxadiazol-5-yl]acetate

A mixture of [3-(4-methoxybenzoyl)-1,2,4-oxadiazol-5-yl]acetonitrile (39 g) in dry isopropanol (1 liter) was saturated with HCl gas. The resulting solution was refluxed for 5 hours, cooled, and poured into cold water (2 liters) with stirring. The aqueous mixture was extracted with Et$_2$O (3×800 ml). The organics were washed with water (4×1 liter) until neutral and saturated NaCl, dried over Na$_2$SO$_4$, and concentrated in vacuo to give 59 g of an oil. The ester crystallized on standing and the supernatant oil was decanted away. The crystals (40 g) were purified by high pressure liquid chromatography (1.5% ethyl acetate/CH$_2$Cl$_2$) to yield 36 g (73%) of an oil which crystallized, m.p. 63°–64°.

ANALYSIS: Calculated for C$_{15}$H$_{16}$N$_2$O$_5$: 59.20%C; 5.31%H; 9.20%N; Found: 59.16%C; 5.36%H; 9.34%N.

EXAMPLE 16

(3-Benzoyl-1,2,4-oxadiazol-5-yl)acetic acid

To a flask containing 8.6 g of isopropyl(3-benzoyl-1,2,4-oxadiazol-5-yl)acetate, which had been cooled in an ice bath, was added 50 ml of cold 97% sulfuric acid. This mixture was swirled continuously for three minutes. The resultant solution was poured gradually into one liter of ice water with mechanical stirring to precipitate the product. The solid was collected by filtration, washed with excess water and dried in vacuo. Recrystallization from acetone/hexane gave 3.5 g (48%) of crystals, m.p. 143°–144.5°.

ANALYSIS: Calculated for C$_{11}$H$_8$N$_2$O$_4$: 56.90%C; 3.47%H; 12.07%N; Found: 56.86%C; 3.43%H; 12.26%N.

EXAMPLE 17

[3-(4-Fluorobenzoyl)-1,2,4-oxadiazol-5-yl]acetic acid

A solution of isopropyl[3-(4-fluorobenzoyl)-1,2,4-oxadiazol-5-yl]acetate (6.2 g) in 97% H$_2$SO$_4$ (40 ml) was stirred at room temperature for 15 minutes. The resulting solution was added slowly to a liter of ice water with mechanical stirring. The precipitated solid was collected by filtration and washed with water (5×300 ml). Drying under vacuum gave 4.4 g of a powder. Recrystallization from 25% hexane/acetone gave 2.5 g (47%) of crystals, m.p. 146°–148°.

ANALYSIS: Calculated for C$_{11}$H$_7$FN$_2$O$_4$: 52.81%C; 2.83%H; 11.19%N; Found: 53.09%C; 2.92%H; 11.25%N.

EXAMPLE 18

[3-(4-Chlorobenzoyl)-1,2,4-oxadiazol-5-yl]acetic acid

To a flask containing 5.2 g of isopropyl [3-(4-chlorobenzoyl)-1,2,4-oxadiazol-5-yl]acetate was added 35 ml of cold concentrated H$_2$SO$_4$. The resulting mixture was stirred and swirled for 15 minutes. The resulting solution was poured slowly into mechanically stirred ice water to precipitate the product. The solid was collected by filtration, washed with excess water and dried under vacuum for 48 hours at room temperature to give 3.9 g of a solid. Recrystallization from acetone/hexane gave 2.5 g (56%) of a solid, m.p. 136°–137°.

ANALYSIS: Calculated for C$_{11}$H$_7$ClN$_2$O$_4$: 49.55%C; 2.65%H; 10.51%N; Found: 49.90%C; 2.91%H; 10.69%N.

EXAMPLE 19

[3-(4-Toluoyl)-1,2,4-oxadiazol-5-yl]acetic acid

To a flask containing 7.0 g of isopropyl [3-(4-toluoyl)-1,2,4-oxadiazol-5-yl]acetate was added 50 ml of cold concentrated sulfuric acid. This mixture was swirled and stirred for 10 minutes. The resulting solution was poured gradually into one liter of ice water with mechanical stirring to precipitate the product. The solid was collected by filtration, washed with water and dried in vacuo at room temperature. Recrystallization from acetone/hexane gave 3.3 g (56%) of a solid, m.p. 140°–141°.

ANALYSIS: Calculated for C$_{12}$H$_{10}$N$_2$O$_4$: 58.53%C; 4.09%H; 11.38%N; Found: 58.51%C; 4.25%H; 11.37%N.

EXAMPLE 20

[3-(4-Methoxybenzoyl)-1,2,4-oxadiazol-5-yl]acetic acid

Finely powdered isopropyl[3-(4-methoxybenzoyl)-1,2,4-oxadiazol-5-yl]acetate (13.5 g) was added in portions over 15 minutes to concentrated H$_2$SO$_4$ (1000 ml) with mechanical stirring. The mixture was stirred an additional 15 minutes until the ester dissolved. The resulting solution was added slowly to ice water (6 liters) with stirring. The precipitated solid was filtered and dissolved in Et$_2$O (1500 ml). The organic phase was washed with water until neutral, saturated NaCl, dried over Na$_2$SO$_4$, and concentrated in vacuo to give 11.0 g of an amorphous solid. The crude acid (7.7 g) was triturated with boiling Et$_2$O (500 ml) to give 3.6 g (45%) of a powder, m.p. 126°–127°.

ANALYSIS: Calculated for C$_{12}$H$_{10}$N$_2$O$_5$: 54.96%C; 3.85%H; 10.68%N; Found: 54.91%C; 3.89%H; 10.76%N.

EXAMPLE 21

4-Chlorobutyl(3-benzoyl-1,2,4-oxadiazol-5-yl)acetate

A solution of 9.7 g of (3-benzoyl-1,2,4-oxadiazol-5-yl)acetonitrile in 250 ml of dry tetrahydrofuran was cooled to −25°. After adding 3.5 ml of ethanethiol, the solution was saturated with HCl gas by continuously bubbling for 15 minutes. The resulting solution was brought to 0° and maintained there for 3 hours. The cold solution was poured into 500 ml of toluene and steam was bubbled directly into the mixture until 200 ml of water had condensed (without cooling). The layers were separated and the organics were washed with water and saturated NaCl solution and dried over MgSO$_4$. Filtration and concentration gave 7 g of an oil. Purification by high pressure liquid chromatography with 11% hexane/CH$_2$Cl$_2$ used as an eluent gave 4.5 g (31%) of an oil.

ANALYSIS: Calculated for C$_{15}$H$_{15}$ClN$_2$O$_4$: 55.82%C; 4.68%H; 8.68%N; Found: 55.89%C; 4.87%H; 8.47%N.

EXAMPLE 22

3-Benzoyl-5-phenylthiomethyl-1,2,4-oxadiazole

A solution of 11.4 ml of triethylamine in 30 ml Et$_2$O was added dropwise to a solution consisting of 9.0 g of 3-benzoyl-5-chloromethyl-1,2,4-oxadiazole, 4.2 ml of thiophenol, 20 ml of acetone and 80 ml of Et$_2$O at room temperature. The resulting mixture was stirred for one hour. The reaction mixture was diluted with Et$_2$O, washed with 5% HCl (2×), water (2×) and brine, and dried over MgSO$_4$. Concentration gave 11.5 g of an oil. Purification by high pressure liquid chromatography with 70% CH$_2$Cl$_2$/hexane as an eluent yielded 10.3 g (84%) of an oil.

ANALYSIS: Calculated for C$_{16}$H$_{12}$N$_2$OS: 64.84%C; 4.08%H; 9.46%N; Found: 64.82%C; 4.20%H; 9.44%N.

EXAMPLE 23

3-(4-Chlorobenzoyl)-5-phenylthiomethyl-1,2,4-oxadiazole

A solution of 8.1 ml of triethylamine in 30 ml Et$_2$O was added to a solution of 7.5 g of 3-(4-chlorobenzoyl)-5-chloromethyl-1,2,4-oxadiazole and 3.0 ml of thiophenol in 20 ml of acetone and 80 ml of Et$_2$O at room temperature. This mixture was stirred for one hour. The reaction mixture was diluted with Et$_2$O, washed with 5% HCl (2×) and brine, and dried over MgSO$_4$. Concentration gave 9.0 g of an oil. Purification by high pressure liquid chromatography with 70% CH$_2$CL$_2$/hexane as an eluent yielded 6.0 g (62%) of an oil.

ANALYSIS: Calculated for C$_{16}$H$_{11}$ClN$_2$O$_2$S: 58.09%C; 3.35%H; 8.47%N; Found: 58.02%C; 3.41%H; 8.34%N.

EXAMPLE 24

5-Phenylthiomethyl-3-(4-toluoyl)-1,2,4-oxadiazole

A solution of 13.4 ml of triethylamine in 35 ml Et$_2$O was added dropwise to a solution of 11.4 g of 5-chloromethyl-3-(4-toluoyl)-1,2,4-oxadiazole and 4.9 ml of thiophenol in 25 ml acetone and 100 ml Et$_2$O at room temperature. The resulting mixture was stirred for one hour. The reaction mixture was diluted with Et$_2$O, washed with 5% HCl (2×), water (2×), and brine, and dried over MgSO$_4$. Concentration gave 13.2 g of an oil. Purification by high pressure liquid chromatography with 70% CH$_2$Cl$_2$/hexane as an eluent yielded 11.0 g (79%) of an oil.

ANALYSIS: Calculated for C$_{17}$H$_{14}$N$_2$O$_2$S: 65.78%C; 4.55%H; 9.03%N; Found: 65.74%C; 4.54%H; 8.96%N.

EXAMPLE 25

3-Benzoyl-5-(phenylsulfinyl)methyl-1,2,4-oxadiazole

A solution of 5.5 g of m-chloroperoxybenzoic acid (85%) in 125 ml of CH$_2$Cl$_2$ was added dropwise at −70° C. under N$_2$ to a solution of 7.5 g of 3-benzoyl-5-phenylthiomethyl-1,2,4-oxadiazole in 150 ml of CH$_2$Cl$_2$. The temperature of the reaction was maintained below −65° by controlling the rate of addition. After stirring further for 30 minutes, the reaction mixture was added directly to a separatory funnel containing 250 ml of 10% Na$_2$S$_2$O$_3$ and 500 ml of Et$_2$O. The organics were washed with saturated NaHCO$_3$ and dried over MgSO$_4$. Concentration gave an oil which solidified on standing. Recrystallization from acetone/hexane gave 3.7 g (44%) of needles, m.p. 79°–81°.

ANALYSIS: Calculated for C$_{16}$H$_{12}$N$_2$O$_3$S: 61.52%C; 3.87%H; 8.97%N; Found: 61.63%C; 3.97%H; 9.16%N.

EXAMPLE 26

3-(4-Chlorobenzoyl)-5-(phenylsulfinyl)methyl-1,2,4-oxadiazole

A solution of 5.8 g of m-chloroperoxybenzoic acid (85%) in 150 ml of CH$_2$Cl$_2$ was added dropwise at −70° under N$_2$ to a solution of 9.0 g of 3-(4-chlorobenzoyl)-5-phenylthiomethyl-1,2,4-oxadiazole in 200 ml of CH$_2$Cl$_2$. The reaction temperature was maintained below −65° by controlling the rate of addition. After stirring further for 30 minutes, the reaction mixture was poured directly into a separatory funnel containing 300 ml of 10% Na$_2$S$_2$O$_3$ and 600 ml of Et$_2$O. The organics were washed with saturated NaHCO$_3$ and dried over MgSO$_4$. Concentration gave an oil which solidified on standing. Recrystallization from acetone/hexane gave 6.7 g (67%) of needles, m.p. 93°–95°.

ANALYSIS: Calculated for C$_{16}$H$_{11}$ClN$_2$O$_3$S: 55.41%C; 3.20%H; 8.08%N; Found: 55.42%C; 3.22%H; 8.20%N.

EXAMPLE 27

5-(Phenylsulfinyl)methyl-3-(4-toluoyl)-1,2,4-oxadiazole

A solution of 5.14 g of m-chloroperoxybenzoic acid (85%) in 125 ml CH$_2$Cl$_2$ was added dropwise to a solution of 7.5 g of 5-phenylthiomethyl-3-(4-toluoyl)-1,2,4-oxadiazole in 150 ml CH$_2$Cl$_2$ at −70° under N$_2$. The temperature was maintained below −65° during the addition by controlling the addition rate and stirring was continued for 30 minutes after the addition while maintaining the temperature below −65°. The resulting mixture was poured directly into a separatory funnel containing 250 ml of 10% Na$_2$S$_2$O$_3$ and 500 ml of Et$_2$O. The organics were washed with saturated NaHCO$_3$ and dried over MgSO$_4$. Concentration gave an oil which solidified on standing. Recrystallization from acetone/hexane gave 5.3 g (64%) of needles, m.p. 97°–99°.

ANALYSIS: Calculated for C$_{17}$H$_{14}$N$_2$O$_3$S: 62.46%C; 4.32%H; 8.57%N; Found: 62.45%C; 4.40%H; 8.74%N.

EXAMPLE 28

(5-Dimethylaminomethyl-1,2,4-oxadiazol-3-yl)-4-fluorophenylmethanone maleate A solution of (5-chloromethyl-1,2,4-oxadiazol-3-yl)-4-fluorophenylmethanone (4.8 g), in 50% Et$_2$O/MeOH (300 ml) at 5° was saturated with dimethylamine gas. The resulting solution was allowed to warm to room temperature and stirred 16 hours. The volatiles were evaporated in vacuo and the residue was taken up in ethyl acetate (250 ml), filtered and concentrated to an oil. The crude amine (6.3 g) was flash chromatographed (25% ethyl acetate/CH$_2$Cl$_2$) to give 2.2 g of an oil.

A solution of the amine in 50% Et$_2$O/CH$_2$Cl$_2$ (20 ml) was added dropwise to a solution of maleic acid (1.2 g, 10 mmol) in Et$_2$O (250 ml). The precipitated salt was filtered and recrystallized from isopropanol (200 ml) to yield 2.4 g (33%) of crystals, m.p. 158°–160°.

ANALYSIS: Calculated for C$_{12}$H$_{12}$FN$_3$O$_2$!$_4$H$_4$O$_4$: 52.60%C; 4.42%H; 11.50%N; Found: 52.49%C; 4.38%H; 11.54%N.

EXAMPLE 29

[5-(Morpholin-4-yl)methyl-1,2,4-oxadiazol-3-yl]-4-fluorophenylmethanone hydrochloride Morpholine (5.5 ml) was added to a solution of (5-chloromethyl-1,2,4-oxadiazol-3-yl)-4-fluorophenylmethanone (4.8 g) in 50% acetone/Et$_2$O (200 ml). The resulting solution was stirred at room temperature for 15 hours. The mixture was filtered and the filtrate concentrated in vacuo to give a residue which was dissolved in Et$_2$O (200 ml). The organic solution was washed with water, and the aqueous washes were extracted with Et$_2$O. The ether solutions were combined, washed with saturated NaCl, dried over Na$_2$SO$_4$, and concentrated in vacuo to give 6.5 g of a solid. The crude residue was flash chromatographed (50% ethyl acetate/hexane) to give 4.5 g of an oil which solidified. A solution of the amine in Et$_2$O was added dropwise to an ethereal HCl solution (600 ml). The precipitated salt was filtered to give 4.0 g and recrystallized from MeOH (300 ml) to yield 2.5 g (38%) of crystals, which decomposed above 210° without melting.

ANALYSIS: Calculated for $C_{14}H_{14}FN_3O_3!HCl$: 51.30%C; 4.62%H; 12.82%N; Found: 51.24%C; 4.69%H; 12.74%N.

EXAMPLE 30

[5-(4-beta-Hydroxyethylpiperazin-1-yl)methyl-1,2,4-oxadiazol-3-yl]-4-fluorophenylmethanone dimaleate A solution of (5-chloromethyl-1,2,4-oxadiazol-3-yl)-4-fluorophenylmethanone (6.0 g) in $Et_2O$ (160 ml) was added to a solution of N-beta-hydroxyethylpiperazine (8.1 g) in MeOH (200 ml). The resulting mixture was stirred at room temperature for 3 days. The solution was concentrated in vacuo to give an oil which was dissolved in $H_2O$ (500 ml). The aqueous solution was extracted with ethyl acetate (6×250 ml) and the organics were combined, washed with saturated NaCl, dried ($Na_2SO_4$), and concentrated in vacuo to give 6.5 g of an oil. The residue was flash chromatographed (4% MeOH/$CH_2Cl_2$) to give 4.0 g of an oil.

A solution of the amine (4.0 g) in $CH_2Cl_2$ (15 ml) was added dropwise to a solution of maleic acid (3.1 g) in $Et_2O$ (500 ml). The precipitated salt was filtered and recrystallized from ethyl acetate (480 ml) to yield 5.0 g (35%) of spherical crystals, m.p. 121°–122°.

ANALYSIS: Calculated for $C_{16}H_{19}FN_4O_3.2(C_4H_4O)$: 50.88%C; 4.81%H; 9.89%N; Found: 50.67%C; 4.96%H; 9.76%N.

EXAMPLE 31

[5-(4-Phenylpiperazin-1-yl)methyl-1,2,4-oxadiazol-3-yl]-4-fluorophenylmethanone

A solution of (5-chloromethyl-1,2,4-oxadiazol-3-yl)-4-fluorophenylmethanone (4.8 g) in acetone (100 ml) was added to a solution of N-phenylpiperazine (9.2 ml) in $Et_2O$ (100 ml). The resulting mixture was stirred at room temperature for 24 hours. The mixture was filtered and the filtrate concentrated in vacuo to give an oil. The crude amine (11 g) was flash chromatographed (8% ethyl acetate/$CH_2Cl_2$) to give 5.6 g of an oil. A second flash chromatography (4% ethyl acetate/$CH_2Cl_2$) yielded 4.1 g (56%) of a solid, m.p. 72°–74°.

ANALYSIS: Calculated for $C_{20}H_{19}FN_4O_2$: 66.56%C; 5.24%H; 15.28%N; Found: 65.56%C; 5.24%H; 15.39%N.

EXAMPLE 32

[5-[4-(2,3,4-Trimethoxybenzyl)piperazin-1-yl]methyl-1,2,4-oxadiazol-3-yl]phenylmethanone dimaleate A solution of 2.4 g of (5-chloromethyl-1,2,4-oxadiazol-3-yl)phenylmethanone in 50 ml of tetrahydrofuran was added to a solution of 7.0 g of N-2,3,4-trimethoxybenzylpiperazine in 50 ml of $CH_3OH$. After stirring the mixture at room temperature for 4 days, it was concentrated to a residue. This material was flash chromatographed with used as an eluent to give 3.8 g of an oil. A solution of this compound in 70 ml of $Et_2O$ was added to a solution of 2.6 g of maleic acid in 400 ml $Et_2O$. The collected solid was recrystallized from ethyl acetate to give 4.5 g (60%) of a solid, m.p. 102°–105°.

ANALYSIS: Calculated for $C_{24}H_{28}N_4O_5.2C_4H_4O_4$: 56.14%C; 5.30%H; 8.18%N; Found: 56.19%C; 5.44%H; 8.22%N.

EXAMPLE 33

[5-[4-(2,3,4-Trimethoxybenzyl)piperazin-1-yl]methyl-1,2,4-oxadiazol-3-yl]-4-tolylmethanone dimaleate A solution of 7.5 g of 2,3,4-trimethoxybenzylpiperazine in 50 ml of $CH_3OH$ was added to a solution of 2.9 g of (5-chloromethyl-1,2,4-oxadiazol-3-yl)-4-tolylmethanone in 50 ml of tetrahydrofuran. The resulting mixture was stirred at room temperature for 3 days. Concentration gave a residue which was flash chromatographed, with 1:2 ethyl acetate/hexane used as an eluent to give 4.1 g of an oil. This was converted to its dimaleate salt in $Et_2O$ and recrystallized from ethyl acetate to give 4.5 g (54%) of a solid, m.p. 129°–130°.

ANALYSIS: Calculated for $C_{25}H_{30}N_4O_5.2C_4H_4O_4$: 56.73%C; 5.48%H; 8.02%N; Found: 56.76%C; 5.49%H; 8.00%N.

EXAMPLE 34

[5-(4-Benzhydrylpiperazin-1-yl)methyl-1,2,4-oxadiazol-3-yl]phenylmethanone dimaleate A solution of (5-chloromethyl-1,2,4-oxadiazol-3-yl)phenylmethanone (2.22 g) in tetrahydrofuran (20 ml) was added to a solution of N-benzhydrylpiperazine (6.3 g) in MeOH (50 ml). The reaction solution was stirred at room temperature for 3 days. The volatiles were evaporated to give a residue which was flash chromatographed (25% ethyl acetate/hexane) to give 4.6 g of an oil.

A solution of the amine in $Et_2O$ (50 ml) was added to a solution of maleic acid (2.6 g) in $Et_2O$ (500 ml). The salt was filtered and recrystallized from ethyl acetate (350 ml) to yield 3.2 g (48%) of crystals, m.p. 133°–135°.

ANALYSIS: Calculated for $C_{27}H_{26}N_4O_2.2(C_4H_4O_4)$: 62.67%C; 5.12%H; 8.35%N; Found: 62.54%C; 5.31%H; 8.27%N.

EXAMPLE 35

[5-(4-Benzhydrylpiperazin-1-yl)methyl-1,2,4-oxadiazol-3-yl]-4-fluorophenylmethanone dimaleate A solution of (5-chloromethyl-1,2,4-oxadiazol-3-yl)-4-fluorophenylmethanone (2.1 g) in tetrahydrofuran (20 ml) was added to a solution of N-benzhydrylpiperazine (5.5 g) in MeOH (50 ml). The reaction solution was stirred at room temperature for 3 days. The volatiles were evaporated to give a residue which was flash chromatographed (25% ethyl acetate/hexane) to give 4.2 g of an oil.

A solution of the amine in $Et_2O$ (40 ml) was added to a solution of maleic acid (2.2 g) in $Et_2O$ (500 ml). The precipitated salt was filtered and recrystallized from EtOAc (200 ml) to yield 3.2 g (53%) of dense crystals, m.p. 146°–148°.

ANALYSIS: Calculated for $C_{27}H_{25}FN_4O_2.2(C_4H_4O_4)$: 61.04%C; 4.84%H; 8.13%N; Found: 61.12%C; 4.89%H; 8.15%N.

EXAMPLE 36

[5-(4-Benzhydrylpiperazin-1-yl)methyl-1,2,4-oxadiazol-3-yl]-4-methoxyphenylmethanone dimaleate A solution of (5-chloromethyl-1,2,4-oxadiazol-3-yl)-4-methoxyphenylmethanone (2.5 g) in tetrahydrofuran (20 ml) was added to a solution of N-benzhydrylpiperazine (6.3 g) in MeOH (50 ml). The reaction solution was stirred at room temperature for 3 days. The volatiles were evaporated to give a residue which was flash chromatographed (25% ethyl acetate/hexane) to give 4.4 g of an oil.

A solution of the amine in CH$_2$Cl$_2$ (20 ml) was added to a solution of maleic acid (2.3 g) in Et$_2$O (700 ml). The precipitated salt was filtered and recrystallized from ethyl acetate (300 ml) to yield 4.4 g (63%) of crystals, m.p. 142°–144°.

ANALYSIS: Calculated for C$_{28}$H$_{28}$N$_4$O$_3$.2(C$_4$H$_4$O$_4$): 61.70%C; 5.19%H; 7.99%N; Found: 61.89%C; 5.21%H; 8.10%N.

EXAMPLE 37

[5-[4-(4,4'-Difluorobenzhydryl)piperazin-1-yl]methyl-1,2,4-oxadiazol-3-yl]phenylmethanone dimaleate A solution of (5-chloromethyl-1,2,4-oxadiazol-3-yl)phenylmethanone (3.0 g) in tetrahydrofuran (20 ml) was added to a solution of N-4,4'-difluorobenzhydryl-piperazine (8.7 g) in MeOH (50 ml). The reaction solution was stirred at room temperature for 3 days. The volatiles were evaporated to give a residue which was flash chromatographed (25% ethyl acetate/hexane) to give 6.5 g of a resin. The residue was purified by high pressure liquid chromatography (2% ethyl acetate/CH$_2$Cl$_2$) to yield 4.1 g of an oil which solidified on standing.

A solution of the amine in CH$_2$Cl$_2$ (30 ml) was added to a solution of maleic acid (2.2 g) in Et$_2$O (400 ml). The precipitated salt was filtered and recrystallized from acetonitrile (100 ml) to yield 5.1 g (54%) of crystals, m.p. 137°–138°.

ANALYSIS: Calculated for C$_{27}$H$_{24}$F$_2$N$_4$O$_2$.2(C$_4$H$_4$O$_4$): 59.48%C; 4.57%H; 7.92%N; Found: 59.32%C; 4.52%H; 7.98%N.

EXAMPLE 38

[5-[4-(4,4'-Difluorobenzhydryl)piperazin-1-yl]methyl-1,2,4-oxadiazol-3-yl]-4-methoxyphenylmethanone dimaleate A solution of [5-chloromethyl-1,2,4-oxadiazol-3-yl]-4-methoxyphenylmethanone (2.5 g) in tetrahydrofuran (20 ml) was added to a solution of N-4,4'-difluorobenzhydrylpiperazine (7.2 g, 25 mmol) in MeOH (60 ml). The reaction solution was stirred at room temperature for 3 days. The volatiles were evaporated to give a residue which was flash chromatographed (25% ethyl acetate/hexane) to give 5.9 g of an oil.

A solution of the amine in CH$_2$Cl$_2$ (40 ml) was added to a solution of maleic acid (2.3 g) in Et$_2$O (600 ml). The precipitated salt was filtered and recrystallized from acetonitrile (175 ml) to yield 3.3 g (45%) of a crystalline powder, m.p. 156°–158°.

ANALYSIS: Calculated for C$_{28}$H$_{26}$F$_2$N$_4$O$_3$.2(C$_4$H$_4$O$_4$): 58.69%C; 4.66%H; 7.60%N; Found: 58.76%C; 4.78%H; 7.71%N.

We claim:

1. A compound having the formula

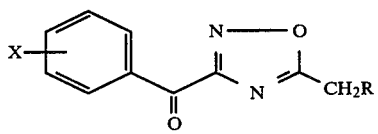

where X is independently hydrogen, halogen (F, Cl, Br or I), loweralkyl or loweralkoxy; and R is —CN, —CONH$_2$, —COOCH(CH$_3$)$_2$, —COOH, —COO(CH$_2$)$_4$Cl,

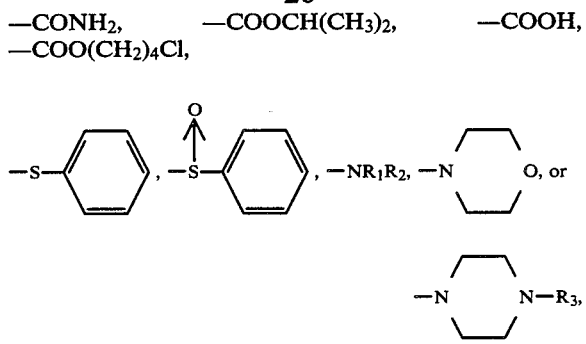

R$_1$ and R$_2$ being independently hydrogen or loweralkyl and R$_3$ being

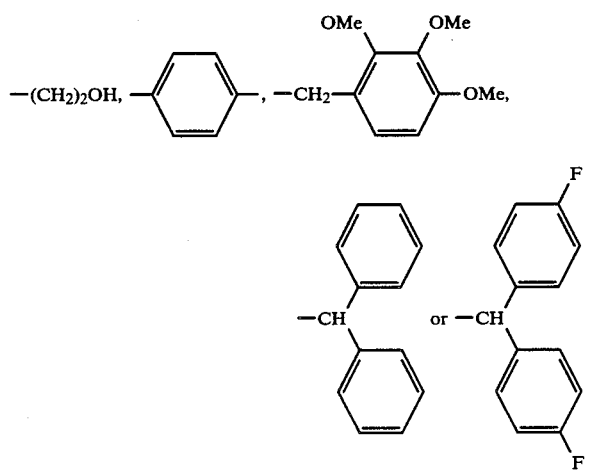

an optical antipode thereof, or a pharmaceutically acceptable acid addition salt thereof.

2. The compound as defined in claim 1, where R is —CN.

3. The compound as defined in claim 2, where X is H, which is (3-benzoyl-1,2,4-oxadiazole-5-yl)acetonitrile.

4. The compound as defined in claim 2, where X is F.

5. The compound as defined in claim 4, where X is 4-fluoro, which is [3-(4-fluorobenzoyl)-1,2,4-oxadiazol-5-yl]acetonitrile.

6. The compound as defined in claim 2, where x is Cl.

7. The compound as defined in claim 6, where x is 4-chloro, which is [3-(4-chlorobenzoyl)-1,2,4-oxadiazol-5-yl]acetonitrile.

8. The compound as defined in claim 2, where X is methyl.

9. The compound as defined in claim 8, where X is 4-methyl, which is [3-(4-toluoyl)-1,2,4-oxadiazol-5-yl]acetonitrile.

10. The compound as defined in claim 2, where X is methoxy.

11. The compound as defined in claim 10, where X is 4-methoxy, which is [3-(4-methoxybenzoyl)-1,2,4-oxadiazol-5-yl]acetonitrile.

12. The compound as defined in claim 1, where R is —CONH$_2$.

13. The compound as defined in claim 12, where X is H, which is (3-benzoyl-1,2,4-oxadiazol-5-yl)acetamide.

14. The compound as defined in claim 12, where X is F.

15. The compound as defined in claim 14, where X is 4-fluoro, which is [3-(4-fluorobenzoyl)-1,2,4-oxadiazol-5-yl]acetamide.

16. The compound as defined in claim 12, where X is Cl.

17. The compound as defined in claim 16, where X is 4-chloro, which is [3-(4-chlorobenzoyl)-1,2,4-oxadiazol-5-yl]acetamide.

18. The compound as defined in claim 12, where X is methyl.

19. The compound as defined in claim 18, where X is 4-methyl, which is [3-(4-Toluoyl)-1,2,4-oxadiazol-5-yl]acetamide.

20. The compound as defined in claim 12, where X is methoxy.

21. The compound as defined in claim 20, where X is 4-methoxy, which is [3-(4-methoxybenzoyl)-1,2,4-oxadiazol-5-yl]acetamide.

22. The compound as defined in claim 1, where R is —COOCH(CH$_3$)$_2$.

23. The compound as defined in claim 22, where X is H, which is isopropyl(3-benzoyl-1,2,4-oxadiazol-5-yl)acetate.

24. The compound as defined in claim 22, where X is F.

25. The compound as defined in claim 24, where X is 4-fluoro, which is isopropyl[3-(4-fluorobenzoyl)-1,2,4-oxadiazol-5-yl]acetate.

26. The compound as defined in claim 22, where X is Cl.

27. The compound as defined in claim 26, where X is 4-chloro, which is isopropyl[3-(4-chlorobenzoyl)-1,2,4-oxadiazol-5-yl]acetate.

28. The compound as defined in claim 22, where X is methyl.

29. The compound as defined in claim 28, where X is 4-methyl, which is isopropyl[3-(4-toluoyl)-1,2,4-oxadiazol-5-yl]acetate.

30. The compound as defined in claim 22, where X is methoxy.

31. The compound as defined in claim 30, where X is 4-methoxy, which is isopropyl[3-(4-methoxybenzoyl)-1,2,4-oxadiazol-5-yl]acetate.

32. The compound as defined in claim 1, where R is —COOH.

33. The compound as defined in claim 32, where X is H, which is (3-benzoyl-1,2,4-oxadiazol-5-yl)acetic acid.

34. The compound as defined in claim 32, where X is F.

35. The compound as defined in claim 34, where X is 4-fluoro, which is [3-(4-fluorobenzoyl)-1,2-4-oxadiazol-5-yl]acetic acid.

36. The compound as defined in claim 32, where X is Cl.

37. The compound as defined in claim 36, where X is 4-chloro, which is [3-(4-chlorobenzoyl)-1,2,4-oxadiazol-5-yl]acetic acid.

38. The compound as defined in claim 32, where X is methyl.

39. The compound as defined in claim 38, where X is 4-methyl, which is [3-(4-toluoyl)-1,2,4-oxadiazol-5-yl]acetic acid.

40. The compound as defined in claim 32, where X is methoxy.

41. The compound as defined in claim 40, where X is 4-methoxy, which is [3-(4-methoxybenzoyl)-1,2,4-oxadiazol-5-yl]acetic acid.

42. The compound as defined in claim 1, where R is —COO(CH$_2$)$_4$Cl.

43. The compound as defined in claim 42, where X is H, which is 4-chlorobutyl(3-benzoyl-1,2,4-oxadiazol-5-yl)acetate.

44. The compound as defined in claim 1, where R is

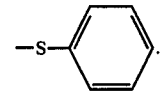

45. The compound as defined in claim 44, where X is H, which is 3-benzoyl-5-phenylthiomethyl-1,2,4-oxadiazole.

46. The compound as defined in claim 44, where X is Cl.

47. The compound as defined in claim 46, where X is 4-chloro, which is 3-(4-chlorobenzoyl)-5-phenylthiomethyl-1,2,4-oxadiazole.

48. The compound as defined in claim 44, where x is methyl.

49. The compound as defined in claim 48, where X is 4-methyl, which is 5-phenylthiomethyl-3-(4-toluoyl)-1,2,3-oxadiazole.

50. The compound as defined in claim 1, where R is

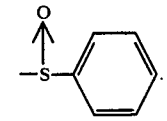

51. The compound as defined in claim 50, where X is H, which is 3-benzoyl-5-(phenylsulfinyl)methyl-1,2,4-oxadiazole.

52. The compound as defined in claim 50, where X is Cl.

53. The compound as defined in claim 52, where X is 4-chloro, which is 3-(4-chlorobenzoyl)-5-(phenylsulfinyl)methyl-1,2,4-oxadiazole.

54. The compound as defined in claim 50, where X is methyl.

55. The compound as defined in claim 54, where X is 4-methyl, which is 5-(phenylsulfinyl)methyl-3-(4-toluoyl)-1,2,4-oxadiazole.

56. The compound as defined in claim 1, where R is —N(CH$_2$)$_2$.

57. The compound as defined in claim 56, where X is F.

58. The compound as defined in claim 57, where X is 4-fluoro, which is (5-dimethylaminomethyl-1,2,4-oxadiazol-3-yl)-4-fluorophenylmethanone.

59. The compound as defined in claim 1, where R is

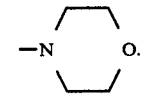

60. The compound as defined in claim 59, where X is F.

61. The compound as defined in claim 60, where X is 4-fluoro, which is [5-(morpholin-4-yl)methyl-1,2,4-oxadiazol-3-yl]-4-fluorophenylmethanone.

62. The compound as defined in claim 1, where R is

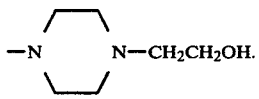

63. The compound as defined in claim 62, where X is F.

64. The compound as defined in claim 63, where X is 4-fluoro, which is [5-(4-beta-hydroxyethylpiperazin-1-yl)methyl-1,2,4-oxadiazol-3-yl]-4-fluorophenylmethanone.

65. The compound as defined in claim 1, where R is

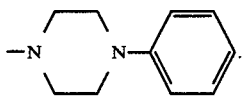

66. The compound as defined in claim 65, where X is F.

67. The compound as defined in claim 66, where X is 4-fluoro, which is [5-(4-phenylpiperazin-1-yl)methyl-1,2,4-oxadiazol-3-yl]-4-fluorophenylmethanone.

68. The compound as defined in claim 1, where R is

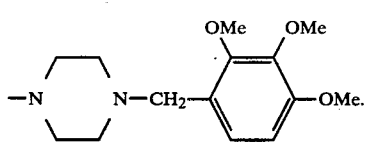

69. The compound as defined in claim 68, where X is H, which is [5-[4-(2,3,4-trimethoxybenzyl)piperazin-1-yl]methyl-1,2,4-oxadiazol-3-yl]phenylmethanone.

70. The compound as defined in claim 68, where X is methoxy.

71. The compound as defined in claim 70, where X is 4-methoxy, which is [5-[4-(2,3,4-trimethoxybenzyl)piperazin-1-yl]methyl-1,2,4-oxadiazol-3-yl]-4-tolylmethanone.

72. The compound as defined in claim 1, where R is

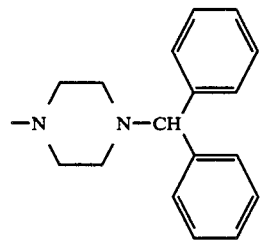

73. The compound as defined in claim 72, where X is H, which is [5-(4-benzhydrylpiperazin-1-yl)methyl-1,2,4-oxadiazol-3-yl]phenylmethanone.

74. The compound as defined in claim 72, where X is F.

75. The compound as defined in claim 74, where X is 4-fluoro, which is [5-(4-benzhydrylpiperazin-1-yl)methyl-1,2,4-oxadiazol-3-yl]-4-fluorophenylmethanone.

76. The compound as defined in claim 72, where X is methoxy.

77. The compound as defined in claim 76, where X is 4-methoxy, which is [5-(4-benzhydrylpiperazin-1-yl)methyl-1,2,4-oxadiazol-3-yl]-4-methoxyphenylmethanone.

78. The compound as defined in claim 1, where R is

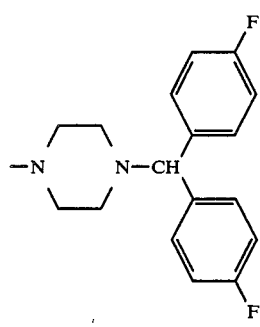

79. The compound as defined in claim 78, where X is H, which is [5-[4-(4,4'-difluorobenzhydryl)piperazin-1-yl]methyl-1,2,4-oxadiazol-3-yl]phenylmethanone.

80. The compound as defined in claim 78, where X is methoxy.

81. The compound as defined in claim 80, where X is 4-methoxy, which is [5-[4-(4,4'-difluorobenzhydryl)piperazin-1-yl]methyl-1,2,4-oxadiazol-3-yl]-4-methoxyphenylmethanone.

82. A pharmaceutical composition comprising an effective amount of a compound defined in claim 1 in association with a carrier or diluent.

83. A method of treating a patient in need of depressing blood pressure which comprises administering to the patient an effective blood pressure depressing amount of a compound defined in claim 1.

84. A method of treating a patient in need of alleviating pain which comprises administering to the patient an effective pain alleviating amount of a compound defined in claim 1.

85. A method of treating a patient in need of suppressing inflammation which comprises administering to the patient an effective inflammation suppressing amount of a compound defined in claim 1.

* * * * *